United States Patent [19]
Lin et al.

[11] Patent Number: 4,898,988
[45] Date of Patent: Feb. 6, 1990

[54] PROCESS FOR THE PREPARATION OF β-HYDROXYKETONES

[75] Inventors: You-Jyh Lin, Columbia; Harold Kloczewski, Pasadena, both of Md.

[73] Assignee: W. R. Grace & Co.-Conn., New York, N.Y.

[21] Appl. No.: 322,259

[22] Filed: Mar. 13, 1989

[51] Int. Cl.$^4$ .............................................. C07C 45/56
[52] U.S. Cl. .................................... 568/386; 568/361; 568/322
[58] Field of Search ......................... 568/386, 361, 322

[56] References Cited

U.S. PATENT DOCUMENTS

| | | | |
|---|---|---|---|
| 3,742,063 | 6/1973 | Hagemeyer, Jr. et al. | 260/347.8 |
| 3,819,714 | 6/1974 | Bluestone et al. | 260/595 |
| 4,226,810 | 10/1980 | Redaelli et al. | 568/386 |
| 4,340,764 | 7/1982 | Milner | 568/386 |
| 4,513,150 | 4/1985 | Fischer et al. | 568/385 |

FOREIGN PATENT DOCUMENTS 47-16434 9/1972 Japan .................................. 568/386

OTHER PUBLICATIONS

Curran, J.A.C.S., vol. 104, pp. 4024–4026 (1982).
Martin et al., Tetrahedron Letters, vol. 24, pp. 1337–1344 (1983).
Kozikowski et al., Chem. Abst., vol. 97, #216,0572 (1982).
"Reduction of Δ$^2$-Isoxazolines. 3.$^1$ Raney–Nickel Catalyzed Formation of β-Hydroxy Ketones"—Curran—*Am. Chem. Soc.*, 1983, 105, 5826–5833.

*Primary Examiner*—James H. Reamer
*Attorney, Agent, or Firm*—James P. Barr

[57] ABSTRACT

A process for the preparation of β-hydroxyketones comprising the catalytic hydrogenolysis of an aqueous solution of isoxazolines having the formula

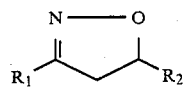

in a fixed bed reactor containing a transition metal catalyst at a temperature between 20° to 150° C. and a pressure from about 0 to 150 psig; wherein $R_1$ and $R_2$ are independently selected from hydrogen, alkyl, cycloalkyl or aromatic group and wherein the aqueous solution of isoxazolines is substantially free of acids or buffers.

9 Claims, No Drawings

PROCESS FOR THE PREPARATION OF β-HYDROXYKETONES

BACKGROUND OF THE INVENTION

1. Field of the Invention

This invention relates to a process for the preparation of β-hydroxyketones by the catalytic hydrogenolysis of 3,5-substituted-isoxazolines using a transition metal catalyst in a fixed bed reactor.

2. Description of the Prior Art

It is known in the prior art that alkyl substituted $\Delta^2$isoxazolines can be catalytically reduced to β-hydroxyketones using Raney nickel catalysts. The general reaction can be expressed as follows:

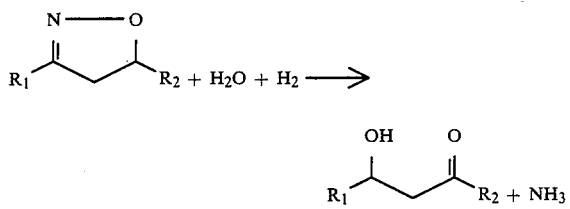

The classical method for preparing β-hydroxyketones involved mixing isoxazoline, acids or buffers, and catalyst to form a slurry, adding the slurry to a reactor (known as a slurry reactor), and constantly agitating the slurry under increased temperature and pressure with addition of hydrogen gas to obtain β-hydroxyketone in from 60 to 90 percent yield. There are, however, several inherent disadvantages to this process.

As indicated in the above reaction, ammonia is a major by-product of this process. Since the prior art process was performed in single batch, slurry reactor, it required the addition of an excess amount of acid or buffer in order to react with the ammonia by-product and thereby avoid deactivation of the catalyst and/or the loss of the selectivity to β-hydroxy ketones.

The addition of acid to a pressurized reactor requires either (1) the use of expensive, non-corrosive acids such as boric acid, or (2) the use of glass-lined reactors suitable for use with corrosive acids such as hydrochloric acid. The excess unreacted acid in this process as well as the slurried catalyst must be removed, thereby increasing the downstream recovery costs.

A further disadvantage of this process is the substantial capital equipment cost attributed to the large reactor size which is required to afford economic feasibility on an industrial scale and which is also necessary to accommodate the agitation equipment required in slurry reactors.

SUMMARY OF THE INVENTION

An object of this invention is to produce β-hydroxyketones in a continuous process.

Another object of this invention is to produce β-hydroxyketones by a process that does not require the addition of buffers or acids.

The β-hydroxyketones are prepared in accordance with this invention by the catalytic hydrogenolysis of isoxazolines using a transition metal catalyst in a fixed bed reactor.

These and other objects will be apparent from the remaining specification and the appended claims.

DETAILED DESCRIPTION

The present invention is directed to a means of providing β-hydroxyketones in high yields by the catalytic hydrogenolysis of isoxazolines having the general formula:

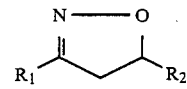

wherein $R_1$ and $R_2$ are each independently selected from hydrogen, alkyl, cycloalkyl or aromatic. The preferred isoxazolines have at least one of the groups $R_1$ and $R_2$ selected from an alkyl group, preferably a $C_1$ to $C_{20}$ alkyl and most preferably a $C_1$ to $C_5$ alkyl group.

Hydrogenolysis of the isoxazolines to form the β-hydroxyketones can be effected by contacting an aqueous solution of isoxazoline with hydrogen in the presence of a catalytic amount of a transition metal catalyst in a fixed bed reactor at temperatures from about 20° to 150° C., preferably from about 20° C. to 50° C., and most preferably at 50° C. and at pressures from about 0 to 150 psig, preferably from about 5 to 80 psig, and is most preferably 80 psig. The concentration of isoxazoline in the aqueous solution is not per se critical to the invention and is limited only by the solubility of isoxazoline in water. The typical concentration is about 5 to 15 weight percent. Preferred transition metal catalysts include nickel, platinum, palladium, rhodium, ruthenium, copper and iridium, and most preferably is a Raney nickel catalyst.

Suitable fixed bed reactors include but are not limited to bubble bed and trickle reactors.

Without further elaboration it is believed that one skilled in the art, using the preceding description, can utilize the present invention to its fullest extent. The following examples are provided to illustrate the invention in accordance with the principles of this invention but are not to be construed as limiting the invention in any way except as indicated in the appended claims. All parts and percentages are by weight unless otherwise indicated.

EXAMPLE 1

This example describes the synthesis of 5-hydroxyhexan-3-one from the catalytic hydrogenolysis of 3-ethyl-5-methylisoxazoline using a transition metal catalyst in a fixed-bed reactor. Three samples of 3-ethyl-5-methylisoxazoline (ISO) were mixed with either water or a water-methanol mixture in varying proportions as indicated in Table 1. This mixture, together with a hydrogen stream, was passed through a tubular fixed-bed reactor having a length of 12 inches and an internal diameter of 0.402 inches, and which contained a Raney nickel catalyst. The flow rate of the liquid reactants was between 0.5 and 0.6 ml/min., while the flow rate of hydrogen was about 300 SCCM (Standard Cubic Centimeters per Minute). The reaction conditions and results are as follows:

TABLE 1

| Sample No. | Liquid Feed Composition (wt. %) | | | Temp. (°C.) | Pressure (psig) | % Conversion | % Selectivity |
| --- | --- | --- | --- | --- | --- | --- | --- |
| | Methanol | Water | ISO | | | | |
| 1 | 81.6 | 13.9 | 4.5 | 20 | 0 | 100 | 71 |
| | | | | 20 | 45 | 100 | 47 |
| | | | | 20 | 80 | 100 | 61 |
| 2 | 13.9 | 81.6 | 4.5 | 20 | 0 | 51 | 77 |
| | | | | 20 | 45 | 100 | 78 |
| | | | | 20 | 80 | 100 | 72 |
| 3 | — | 87 | 13 | 20 | 0 | 29 | 80 |
| | | | | 20 | 45 | 44 | 82 |
| | | | | 20 | 80 | 51 | 82 |
| | | | | 50 | 45 | 77 | 82 |
| | | | | 50 | 80 | 100 | 81 |

As is evident from the above results, β-hydroxyketones can be prepared successfully using a transition metal catalyst in a fixed-bed reactor with the following advantages over the slurry reactor:
(1) no acid is required.
(2) no methanol is required, since water can serve as both a solvent and a reactant.
(3) the throughput of β-hydroxyketones can be increased by increasing the solubility of the isoxazoline in the reactant stream while the conversion and selectivity are maintained.

What is claimed is:

1. A process for the preparation of β-hydroxyketones comprising: the catalytic hydrogenolysis of an aqueous solution of isoxazolines having the formula

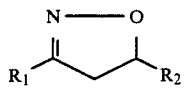

together with a stream of hydrogen in a fixed-bed reactor containing a transition metal catalyst at a temperature from about 20° to 150° C. and a pressure from about 0 to 150 psig; wherein $R_1$ and $R_2$ are independently selected from hydrogen, alkyl, cycloalkyl or aromatic group; and wherein the aqueous solution of isoxazolines is substantially free of acids or buffers.

2. The process according to claim 1 wherein $R_1$ and $R_2$ are independently selected from a $C_1$ to $C_{20}$ alkyl.

3. The process according to claim 1 wherein $R_1$ and $R_2$ are independently selected from methyl or ethyl.

4. The process according to claim 1, wherein the transition metal catalyst is selected from the group of nickel, platinum, palladium, rhodium, ruthenium, copper, and iridium.

5. The process according to claim 1, wherein the transition metal catalyst is Raney nickel.

6. The process according to claim 1, wherein the temperature is between 20° and 50° C.

7. The process according to claim 1, wherein the pressure is from 5 to 80 psig.

8. A process for the preparation of β-hydroxyketones comprising: the catalytic hydrogenolysis of an aqueous solution of isoxazolines having the formula:

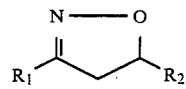

together with a stream of hydrogen in a fixed bed reactor containing a Raney nickel catalyst at a temperature about 50° C. and a pressure about 80 psig; wherein $R_1$ and $R_2$ are independently selected from methyl or ethyl; and wherein the aqueous solution of isoxazolines is substantially free of acids or buffers.

9. A continuous process for the preparation of β-hydroxyketones comprising the steps of: forming an aqueous solution of isoxazolines having the formula

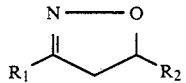

wherein $R_1$ and $R_2$ are independently selected from hydrogen, alkyl, cycloalkyl and aromatic group; passing the solution, together with a stream of hydrogen through a fixed bed reactor containing a transition metal catalyst at a temperature from about 20° to 150° C. and a pressure from about 0 to 150 psig, to form β-hydroxyketones having the formula

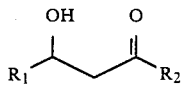

wherein $R_1$ and $R_2$ have the above meaning.

* * * * *